(12) United States Patent
Hsiao et al.

(10) Patent No.: US 10,100,017 B2
(45) Date of Patent: Oct. 16, 2018

(54) PROCESSES FOR PREPARING OLAPARIB

(71) Applicant: SCINOPHARM TAIWAN, LTD., Tainan (TW)

(72) Inventors: Tsung-Yu Hsiao, Kaohisiung (TW); Yung-Hung Chang, Taichung (TW)

(73) Assignee: SCINOPHARM TAIWAN, LTD., Tainan (TW)

( * ) Notice: Subject to any disclaimer, the term of this patent is extended or adjusted under 35 U.S.C. 154(b) by 0 days.

(21) Appl. No.: 15/684,222

(22) Filed: Aug. 23, 2017

(65) Prior Publication Data

US 2018/0057464 A1 Mar. 1, 2018

Related U.S. Application Data

(60) Provisional application No. 62/379,026, filed on Aug. 24, 2016.

(51) Int. Cl.
*C07D 237/32* (2006.01)
(52) U.S. Cl.
CPC .................................. *C07D 237/32* (2013.01)
(58) Field of Classification Search
CPC .................................................... C07D 237/32
USPC ......................................................... 544/237
See application file for complete search history.

(56) References Cited

U.S. PATENT DOCUMENTS

| 7,449,464 | B2 | 11/2008 | Martin et al. |
| 7,692,006 | B2 | 4/2010 | Menear et al. |
| 8,247,416 | B2 | 8/2012 | Menear et al. |

FOREIGN PATENT DOCUMENTS

| CN | 103172619 A | 6/2013 |
| CN | 105820126 A | 8/2016 |
| WO | WO-2004/080976 A1 | 9/2004 |
| WO | WO-2018/038680 A1 | 3/2018 |

OTHER PUBLICATIONS

International Search Report dated Dec. 27, 2017, for PCT/SG2017/050402, filed Aug. 11, 2017, 5 pages.
Written Opinion dated Dec. 27, 2017, for PCT/SG2017/050402, filed Aug. 11, 2017, 6 pages.
Zmuda, F. et al. (Nov. 12, 2015, e-published Oct. 27). "Synthesis and Evaluation of a Radioiodinated Tracer with Specificity for Poly(ADP-ribose) Polymerase-1 (PARP-1) in Vivo," *J Med Chem* 58(21):8683-8693.

*Primary Examiner* — Kahsay Habte
(74) *Attorney, Agent, or Firm* — Mintz, Levin, Cohn, Ferris, Glovsky and Popeo, P.C.

(57) ABSTRACT

Provided herein are novel processes and methods for making 4-[(3-[(4-cyclopropylcarbonyl)piperazin-1-yl]carbonyl)-4-fluorophenyl]methyl(2H)phthalazin-1-one (Olaparib) and intermediates thereof. Olaparib is a poly ADP ribose polymerase (PARP) inhibitor useful in the treatment of cancers. Benefits of the present disclosure include the use of less toxic compounds and improved yields.

15 Claims, No Drawings

US 10,100,017 B2

PROCESSES FOR PREPARING OLAPARIB

CROSS-REFERENCES TO RELATED APPLICATIONS

This application claims the benefit of priority to U.S. Provisional Application Ser. No. 62/379,026 filed Aug. 24, 2016, the entirety of which is incorporated herein by reference for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Olaparib (AZD-2281, trade name Lynparza) is an FDA-approved targeted therapy for cancer, developed by KuDOS Pharmaceuticals and later by AstraZeneca. Lynparza is approved in the form of 50 mg capsules. It is a PARP inhibitor, inhibiting poly ADP ribose polymerase (PARP), an enzyme involved in DNA repair. It acts against cancers in people with hereditary BRCA1 or BRCA2 mutations, which include some ovarian, breast, and prostate cancers. In December 2014, Olaparib was approved for use as a single agent by the EMA and the FDA. The FDA approval is in for germline BRCA mutated (gBRCAm) advanced ovarian cancer that has received three or more prior lines of chemotherapy. The prescribing information instructs physicians to "select patients for the treatment of advanced ovarian cancer with Lynparza based on the presence of deleterious or suspected deleterious germline BRCA-mutations."

AstraZeneca recently announced that FDA has granted Breakthrough Therapy Designation (BTD) for the oral poly ADP-ribose polymerase (PARP) inhibitor Lynparza™ (olaparib), for the monotherapy treatment of BRCA1/2 or ATM gene mutated metastatic Castration Resistant Prostate Cancer (mCRPC) in patients who have received a prior taxane-based chemotherapy and at least one newer hormonal agent (abiraterone or enzalutamide).

Given the great usefulness of this compound, a need in the art exists to effectively and efficiently synthesize olaparib.

A key intermediate in the process of preparing olaparib is 2-fluoro-5-((4-oxo-3,4-dihydro-phthalazin-1-yl)methyl)-benzoic acid (compound D). Two synthetic approaches of olaparib are the main design developed by this company and they are disclosed or claimed in the U.S. Pat. Nos. 7,449,464, 7,692,006 and 8,247,416. Scheme 1, below, illustrates the synthetic schemes describes in these patents.

Scheme 1: Preparation of Olaparib Disclosed in U.S. Pat. Nos. 7,449,464; 7,692,006; and 8,247,416

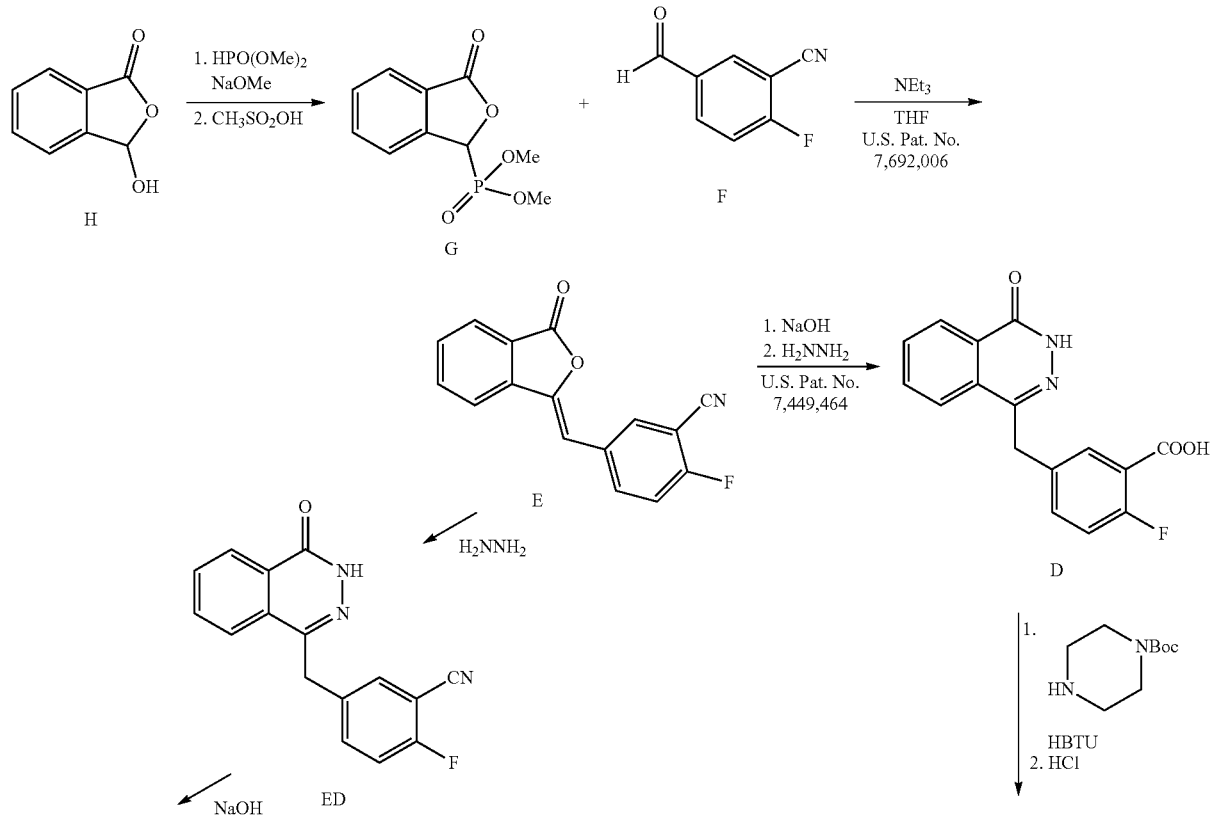

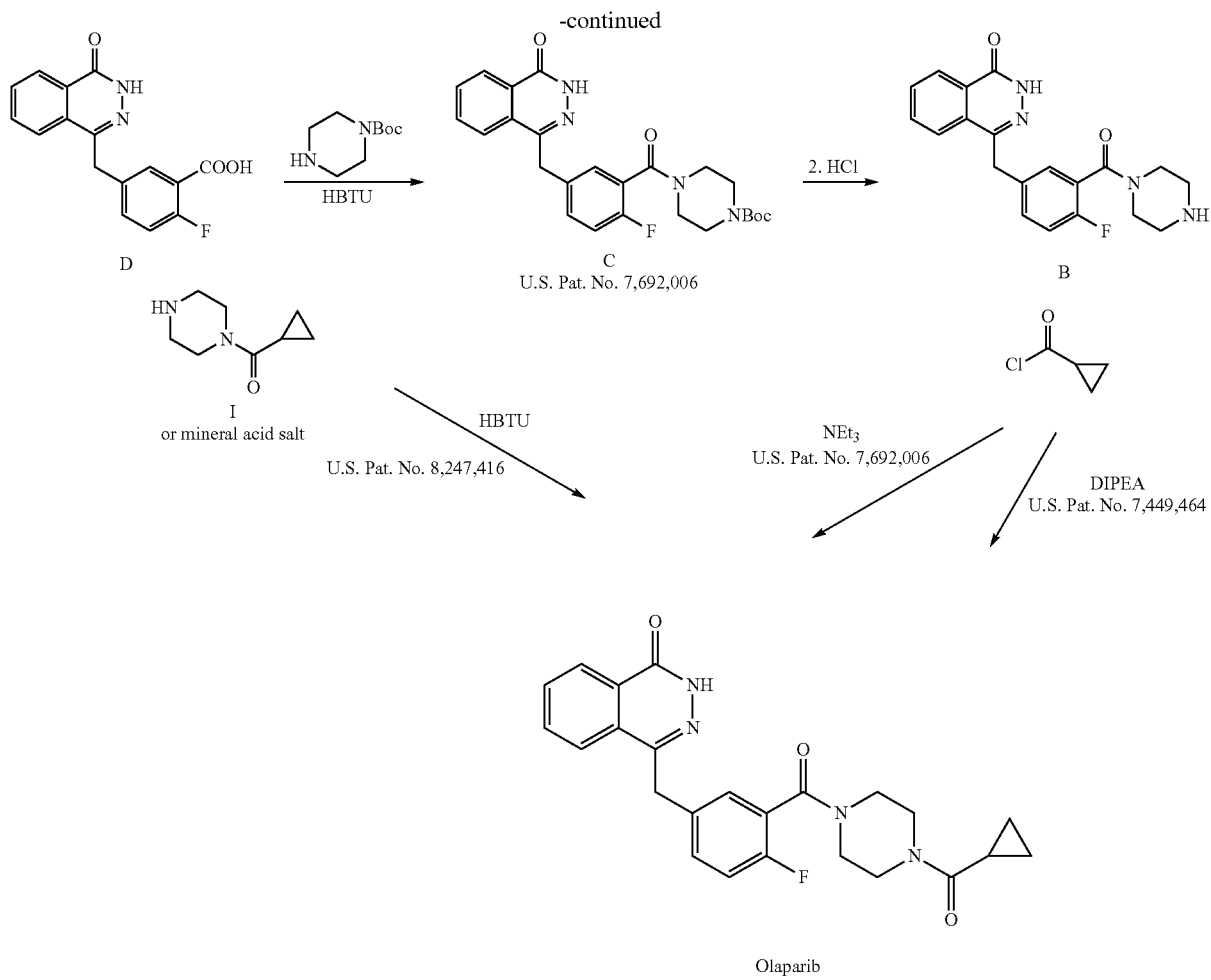

The '006 approach involves contacting compound D with 1-Boc-piperazine in dimethylacetamine (DMA) in the presence of HBTU (2-(1H-benzotriazol-1-yl)-1,1,3,3-tetramethyluronium hexafluorophosphate) to provide 4-[2-fluoro-5-(4-oxo-3,4-dihydro-phthalazin-1-ylmethyl)-benzoyl]-piperazin-1-carboxylic acid tert-butyl ester (compound C), followed by adding concentrated HCl to remove tert-butoxycarbonyl (Boc) group and obtaining 4-[4-fluoro-3-(piperazine-1-carbonyl)benzyl]-2H-phthalazin-1-one (compound B), and then compound B couples with cyclopropane carbonyl chloride to afford crude 4-[3-(4-cyclocarbonyl-piperazine-1-carbonyl)-4-fluoro-benzyl]-2H-phthalazin-1-one (i.e., crude olaparib).

The '416 approach is related to a direct coupling reaction of compound D with 1-(cyclopropylcarbonyl)piperazine (compound I) or 1-(cyclopropylcarbonyl)piperazine HCl salt (compound I') in the presence of HBTU to obtain crude olaparib (Scheme 1).

According to the above-mentioned '006 approach, treatment of compound D with 1-Boc-piperazine in dimethylacetamide (DMA) in the presence of an expensive (and difficult to dissolve) amide coupling reagent 2-(1H-benzotriazol-1-yl)-1,1,3,3-tetramethyluronium hexafluorophosphate (HBTU) resulted in the formation of compound C with only a 78% yield.

See, Scheme 2.

Scheme 2: Synthesis of compound C from compound D

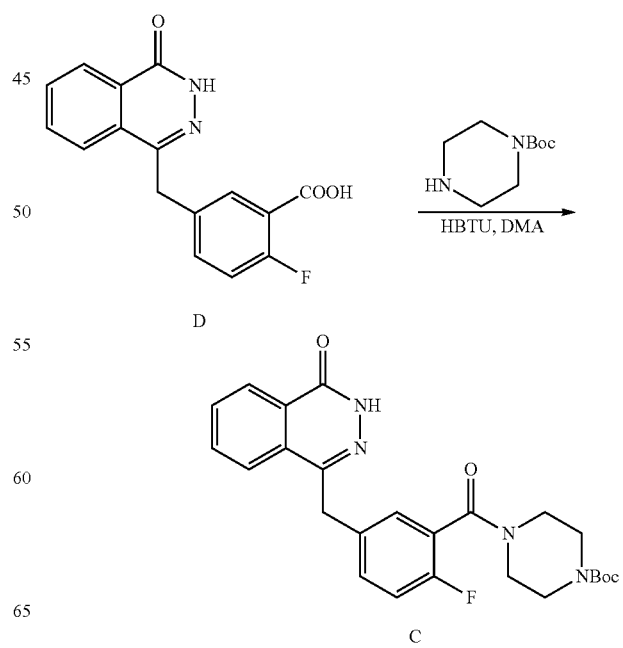

In the next step of the '006 approach, compound C underwent de-Boc reaction under acidic conditions (concentrated HCl$_{(aq)}$ in MeOH) to afford compound B with a yield of only 58.50% yield. See, Scheme 3.

Scheme 3: Synthesis of compound B from compound C

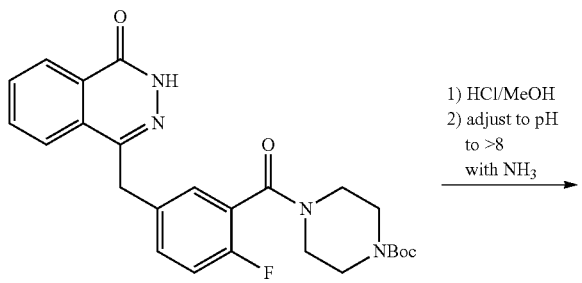

Subsequently, a pre-mixed solution of triethylamine (Et$_3$N) and cyclopropane carbonyl chloride in dichloromethane was added dropwise to a stirred solution of compound B in dichloromethane. Upon completion, the reaction mixture was extracted with 5% citric acid$_{(aq)}$, 5% Na$_2$CO$_{3(aq)}$, and water, followed by distilling dichloromethane and replacing the distillate with ethanol. The resulting mixture was filtered and the solid was recrystallized in water to afford olaparib in 90% yield. See, Scheme 4. However, this reaction includes the use of toxic chemicals such as dichloromethane and requires distilling the solvent in the work up steps.

Scheme 4: Synthesis of Olaparib from compound B

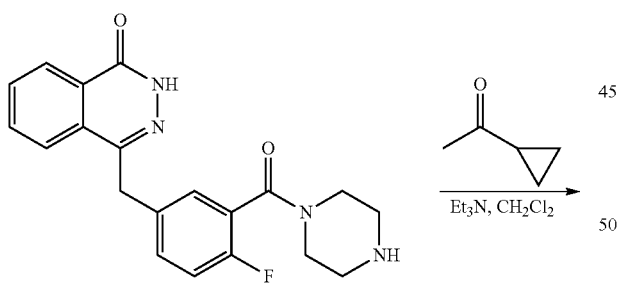

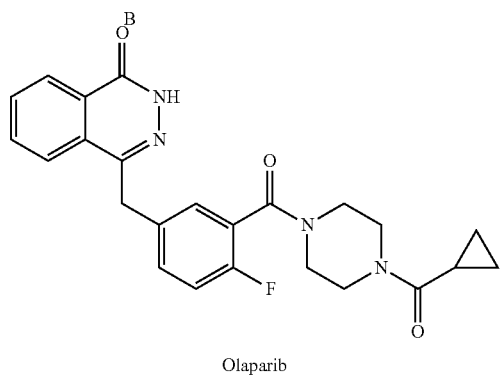

Olaparib

According to the '416 approach, treatment of compound D with 1-(cyclopropylcarbonyl)piperazine or its mineral acid salt in the presence of an amide coupling reagent 2-(1H-benzotriazol-1-yl)-1,1,3,3-tetramethyluronium hexafluorophosphate (HBTU) and a base in acetonitrile led to the formation of olaparib directly. See, Scheme 5. However, the process described in the '416 patent only affords olaparib in 84% or 62% yields after recrystallization. Moreover, this reaction includes the use of an expensive (and difficult to dissolve) coupling agent (HBTU) as well as a toxic and highly flammable solvent in acetonitrile.

Scheme 5: Synthesis of Olaparib from compound D by using compound I or I'.

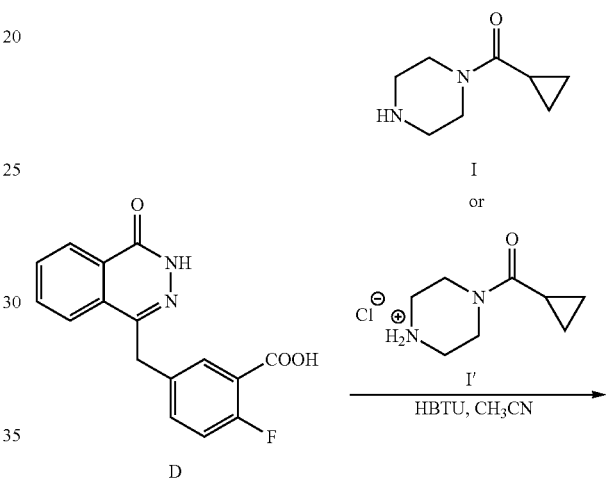

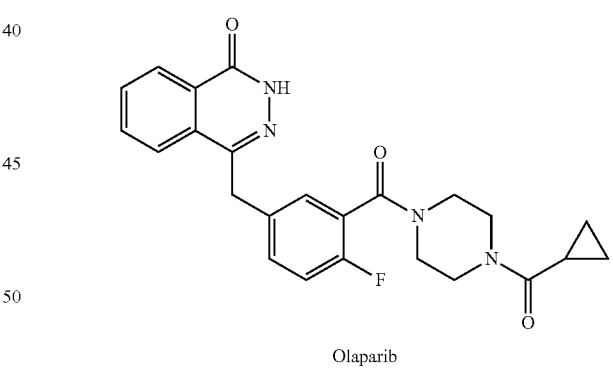

Olaparib

In view of the foregoing, the need exists for an improved process to produce olaparib with commercially acceptable yields, increased efficiency, and less toxic chemicals.

BRIEF SUMMARY OF THE INVENTION

In a first aspect, the present disclosure provides a process for preparing 4-[(3-[(4-cyclopropylcarbonyl)piperazin-1-yl]carbonyl)-4-fluorophenyl]methyl(2H)phthalazin-1-one (Olaparib)

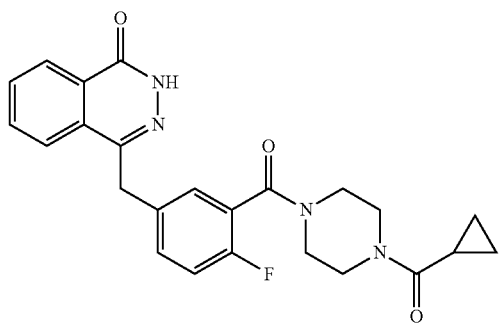 [SMILES: O=C(c1cc(Cc2n[nH]c(=O)c3ccccc23)ccc1F)N1CCN(C(=O)C2CC2)CC1]

comprising the steps of (a) contacting 5-[(3,4-dihydro-4-oxo-1-phthalazinyl)methyl]-2-fluorobenzoic acid (compound D):

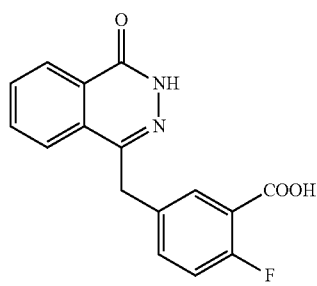

D with 1-(tert-butoxycarbonyl)piperazine, pivaloyl chloride, and a tertiary amine in a first organic solvent to provide compound C

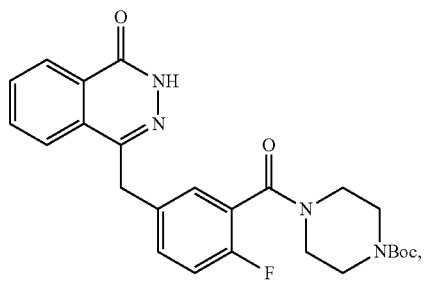

C (b) contacting compound C and an acid to provide compound L

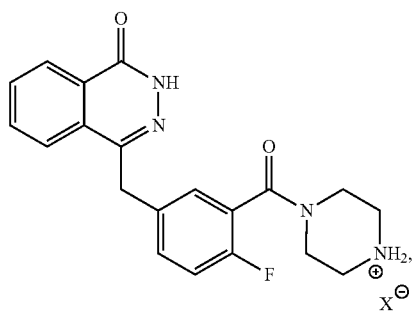

L wherein X is an anion; and (c) contacting compound L with cyclopropanecarbonyl chloride and an inorganic base in a biphasic reaction system comprising water and a second organic solvent to afford olaparib.

In a second aspect, the present disclosure provides a process for preparing tert-butyl 4-(2-fluoro-5-((4-oxo-3,4-dihydrophthalazin-1-yl)methyl)benzoyl)piperazine-1-carboxylate (compound C)

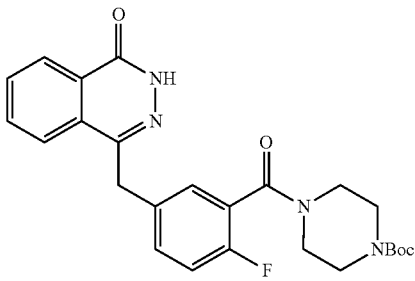

C comprising:

(a) contacting 5-[(3,4-dihydro-4-oxo-1-phthalazinyl)methyl]-2-fluorobenzoic acid (compound D):

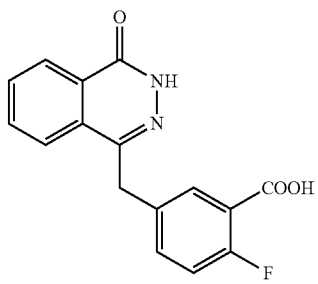

D with 1-(tert-butoxycarbonyl)piperazine, pivaloyl chloride and a tertiary amine in a first organic solvent to provide compound C.

In a third aspect, the present disclosure provides a process for preparing compound L

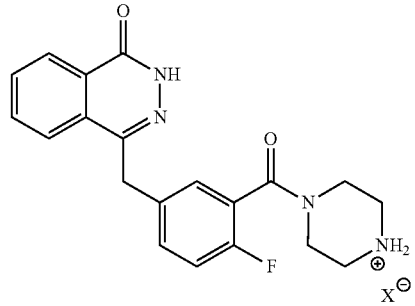

L comprising:

(b) contacting compound C

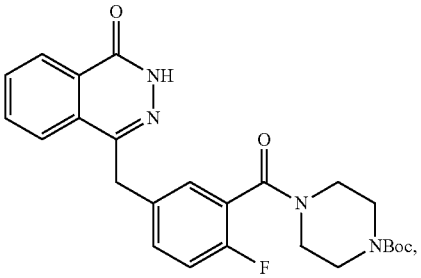

C and an acid to provide compound L, wherein X is an anion.

In a fourth aspect, the present disclosure provides a process for preparing 4-[(3-[(4-cyclopropylcarbonyl)piperazin-1-yl]carbonyl)-4-fluorophenyl]methyl(2H)phthalazin-1-one (Olaparib)

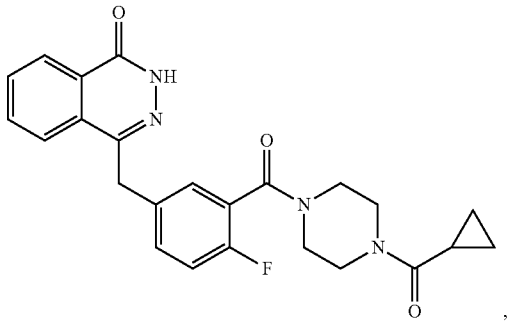 [SMILES: O=C(c1cc(Cc2n[nH]c(=O)c3ccccc23)ccc1F)N1CCN(C(=O)C2CC2)CC1 ; ","]

comprising:
(c) contacting compound L or its free base

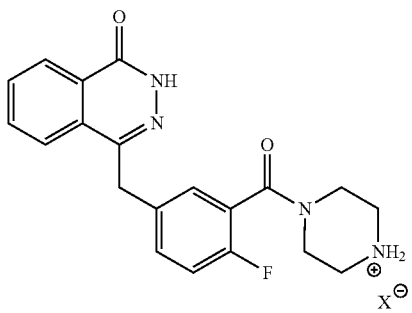

with cyclopropanecarbonyl chloride and an inorganic base in a biphasic reaction system comprising water and a second organic solvent to afford olaparib, wherein X is an anion.

In some embodiments of the first and second aspects of the present disclosure, the tertiary amine is selected from the group consisting of trimethylamine, N,N-diisopropylethylamine (DIPEA), N-methylmorpholine (NMM), tributylamine, 2,2,6,6-tetramethylpiperidine (TMP), pempidine (PMP), 2,6-dimethylpyridine, 2,4,6-trimethylpyridine.

In some embodiments of the first and second aspects of the present disclosure, the tertiary amine is N,N-diisopropylethylamine (DIPEA).

In some embodiments of the first and second aspects of the present disclosure, the first organic solvent is a dialkyl ketone. In some embodiments, the dialkyl ketone is selected from the group consisting of acetone, acetophenone, butanone, diethyl ketone, ethyl isopropyl ketone, 2-hexanone, isophorone, mesityl oxide, methyl isobutyl ketone, methylisopropyl ketone, 3-methyl-2-pentanone, 2-pentanone, cyclohexanone, and cyclopetanone. In some embodiments the dialkyl ketone is acetone.

In some embodiments of the first and third aspects of the present disclosure, the acid used in step (b) is p-toluenesulfonic acid.

In some embodiments of the first and third aspects of the present disclosure, the anion is tosylate.

In some embodiments of the first and fourth aspect of the present disclosure, the inorganic base used in step (c) is selected from a group consisting of an alkali metal carbonate, an alkali metal bicarbonate, and combinations thereof. In some embodiments, the alkali metal carbonate is selected from the group consisting of $Li_2CO_3$, $Na_2CO_3$, $K_2CO_3$, and combinations thereof. In some embodiments, the alkali metal carbonate is $K_2CO_3$. In some embodiments, the alkali metal bicarbonate is selected from the group consisting of $LiHCO_3$, $NaHCO_3$, and combinations thereof.

In some embodiments of the first and fourth aspect of the present disclosure, the second organic solvent is a $C_{1-10}$alkyl acetate. In some embodiments, the $C_{1-10}$alkyl acetate is ethyl acetate.

In some embodiments of the first aspect of the present disclosure, steps (a) and (b) are performed in a single reaction vessel. In some embodiments, said acid is directly added to said reaction vessel to provide compound L.

In a fifth aspect, the present disclosure provides a process for preparing 4-[(3-[(4-cyclopropylcarbonyl)piperazin-1-yl]carbonyl)-4-fluorophenyl]methyl(2H)phthalazin-1-one (Olaparib)

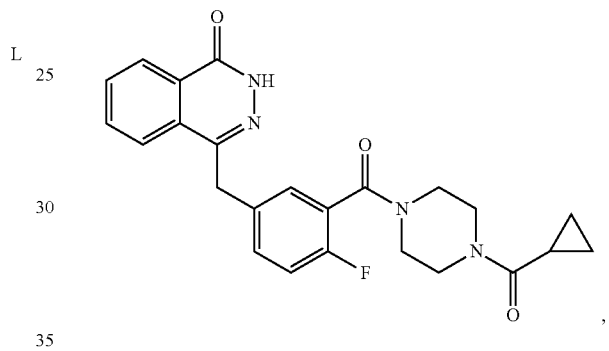

comprising contacting the 5-[(3,4-dihydro-4-oxo-1-phthalazinyl)methyl]-2-fluorobenzoic acid (compound D):

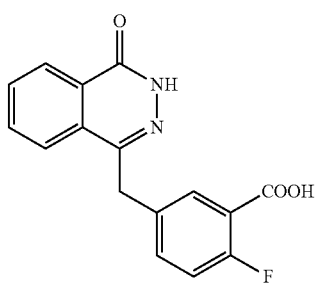

with N-cyclopropanoyl piperazinium p-toluenesulfonate (compound A)

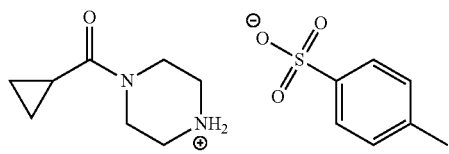

pivaloyl chloride and a tertiary amine in an organic solvent to afford olaparib.

In some embodiments of the fifth aspect of the present disclosure, the tertiary amine is selected from the group consisting of trimethylamine, N,N-diisopropylethylamine (DIPEA), N-methylmorpholine (NMM), tributylamine, 2,2,6,6-tetramethylpiperidine (TMP), pempidine (PMP), 2,6-dimethylpyridine, 2,4,6-trimethylpyridine.

In some embodiments of the fifth aspect of the present disclosure, the tertiary amine is N,N-diisopropylethylamine (DIPEA).

In some embodiments of the fifth aspect of the present disclosure, the organic solvent is a dialkyl ketone. In some embodiments, the dialkyl ketone is selected from the group consisting of acetone, acetophenone, butanone, diethyl ketone, ethyl isopropyl ketone, 2-hexanone, isophorone, mesityl oxide, methyl isobutyl ketone, methylisopropyl ketone, 3-methyl-2-pentanone, 2-pentanone, cyclohexanone, and cyclopetanone. In some embodiments, the dialkyl ketone is acetone.

DETAILED DESCRIPTION OF THE INVENTION

I. General

The present invention provides improved processes for the preparation of 4-[(3-[(4-cyclopropylcarbonyl)piperazin-1-yl]carbonyl)-4-fluorophenyl]methyl(2H)phthalazin-1-one (Olaparib) and intermediates thereof. Olaparib is a poly ADP ribose polymerase (PARP) inhibitor, and is useful in the treatment of cancer. Olaparib can be particularly useful as a cancer treatment in people with hereditary BRCA1 or BRCA2 mutations, which include some ovarian, breast, and prostate cancers.

More specifically, the present disclosure provides two improved chemical process for the preparation of olaparib and intermediates thereof. Each route involves the use of the compound 2-fluoro-5-((4-oxo-3,4-dihydro-phthalazin-1-yl)methyl)-benzoic acid (compound D) as a starting material in the preparation of olaparib. Each step in both disclosed processes provides advancements over known methods such as improved yields, improved purities, use of less toxic reagents and solvents, and/or provides more efficient isolation of relatively high purity olaparib. Accordingly, the present invention is time-saving, more environmentally friendly, and suitable for industrial manufacturing.

While a complete synthetic scheme is provided in the description of the embodiments (see, Scheme 6), one of skill in the art will appreciate that selected steps of the instant process are novel and can be performed independent of the origin of the starting material or intermediates.

II. Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the terms "tosylate" or "p-toluenesulfonate" refers to the anion of p-toluenesulfonic acid ($CH_3C_6H_4SO_3^-$). The term may also be abbreviated as $TsO^-$.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "biphasic reaction system" refers to a reaction system having two phases. An example of a biphasic reaction system is one containing an aqueous phase and an organic phase.

III. Embodiments of the Invention

There are two synthetic routes of the present invention included in the present application. As used herein, the first route of the present invention is called "Route A" and the other is called "Route B". See, Scheme 6.

Scheme 6: Preparation of Olaparib-Routes A and B
Route A

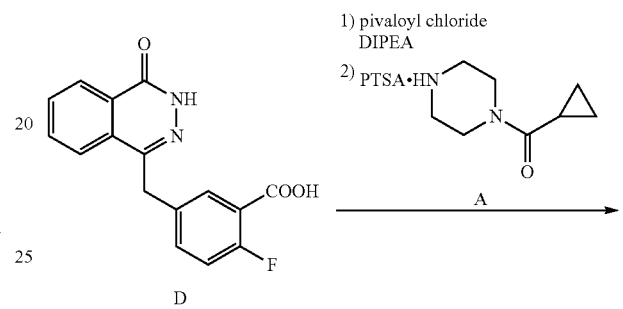

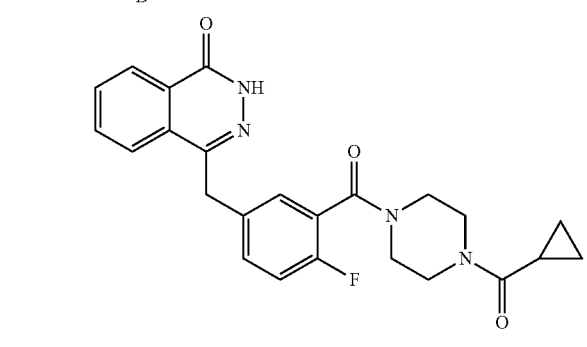

Olaparib

Route B

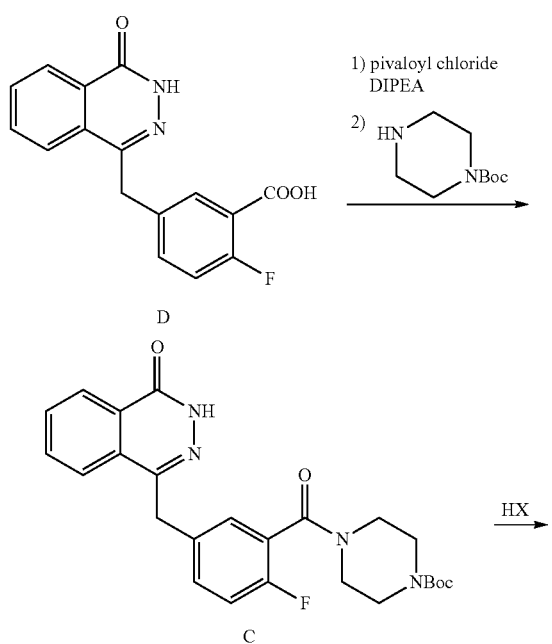

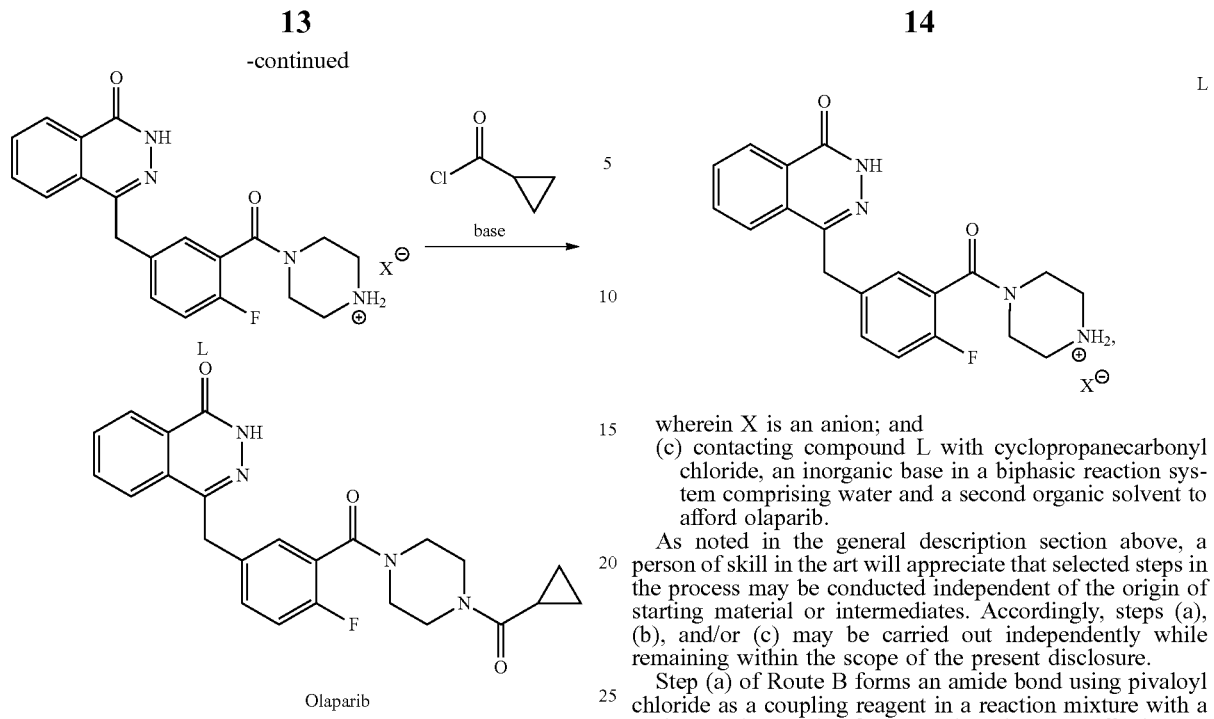

A. Route B

In accordance with Route B of the present disclosure, the synthesis of olaparib can be performed by (a) contacting 5-[(3,4-dihydro-4-oxo-1-phthalazinyl)methyl]-2-fluorobenzoic acid (compound D):

with 1-(tert-butoxycarbonyl)piperazine, pivaloyl chloride, and a tertiary amine in a first organic solvent to provide compound C (b) contacting compound C and a suitable acid to provide compound L wherein X is an anion; and (c) contacting compound L with cyclopropanecarbonyl chloride, an inorganic base in a biphasic reaction system comprising water and a second organic solvent to afford olaparib.

As noted in the general description section above, a person of skill in the art will appreciate that selected steps in the process may be conducted independent of the origin of starting material or intermediates. Accordingly, steps (a), (b), and/or (c) may be carried out independently while remaining within the scope of the present disclosure.

Step (a) of Route B forms an amide bond using pivaloyl chloride as a coupling reagent in a reaction mixture with a tertiary amine, and a first organic solvent to afford compound C. See, Scheme 8. The embodiments of step (a) described herein not only improve the yield of this conversion, but also use a cheaper coupling reagent making the process more industrially applicable.

Scheme 8: Synthesis of C Using Pivaloyl Chloride as Coupling Reagent

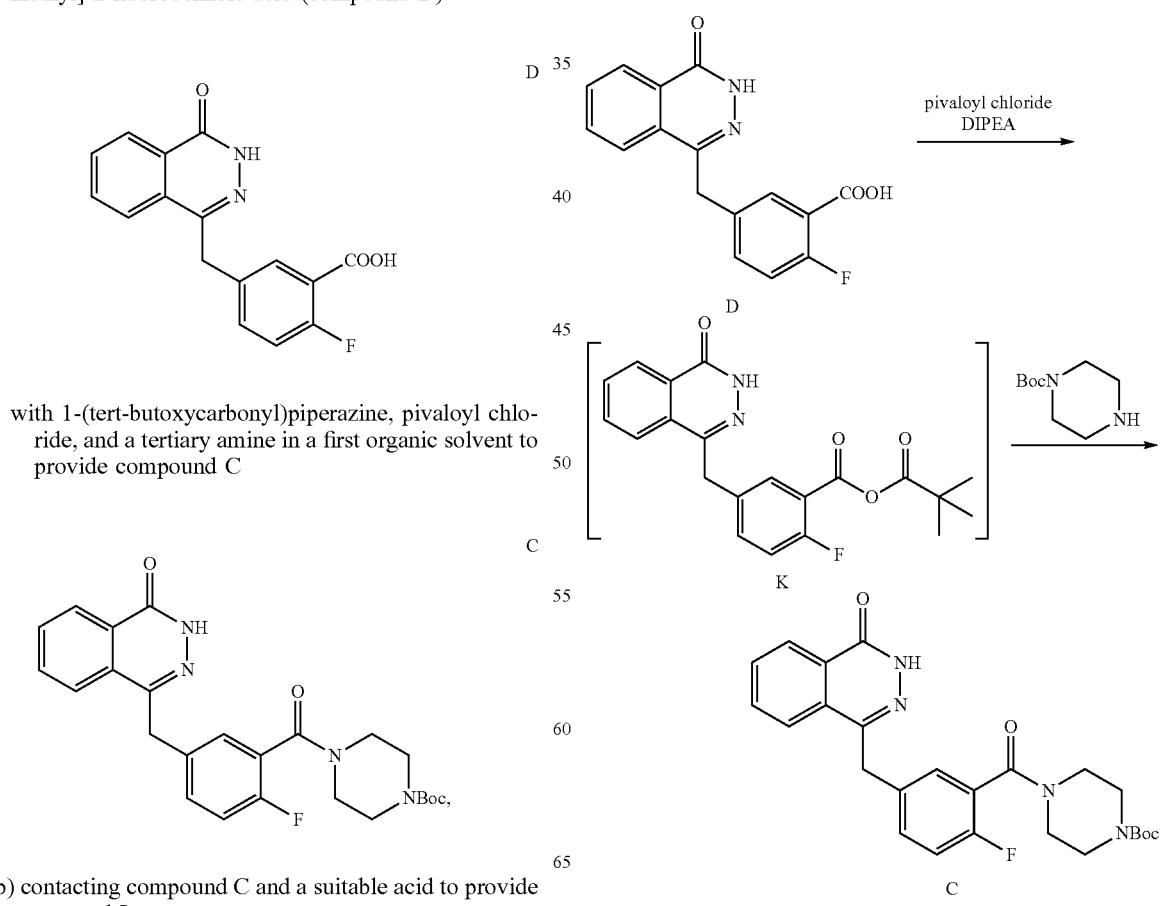

A particular order of addition of compounds and solvents is not required in successfully converting compound D to compound C. Typically, one would admix compound D dissolved in an organic solvent with DIPEA and pivaloyl chloride. After a suitable amount of time, 1-(tert-butoxycarbonyl)piperazine is added to this reaction mixture. In some embodiments, all reagents and solvents are added simultaneously.

The conversion of compound D to compound C according to step (a) of Route B can be carried out at a variety of temperatures. For example, the reaction can be performed at from about 5 to 100° C., from about 10 to 60° C., from about 15 to 40° C., or from about 20 to 30° C. In some embodiments, the addition of DIPEA is performed at a temperature of not more than 30° C. A person of skill in the art will recognize the time to complete the reaction will depend on temperature.

In some embodiments, the tertiary amine used in step (a) of Route B is selected from the group consisting of trimethylamine, N,N-diisopropylethylamine (DIPEA), N-methylmorpholine (NMM), tributylamine, 2,2,6,6-tetramethylpiperidine (TMP), pempidine (PMP), 2,6-dimethylpyridine, 2,4,6-trimethylpyridine. In some embodiments, the tertiary amine used in step (a) is N,N-diisopropylethylamine (DIPEA).

In some embodiments, the first organic solvent used in step (a) of Route B is a dialkyl ketone. In some embodiments, the dialkyl ketone is selected from the group consisting of acetone, acetophenone, butanone, diethyl ketone, ethyl isopropyl ketone, 2-hexanone, isophorone, mesityl oxide, methyl isobutyl ketone, methylisopropyl ketone, 3-methyl-2-pentanone, 2-pentanone, cyclohexanone, and cyclopetanone. In some embodiments the dialkyl ketone is acetone.

In some embodiments, the yield of step (a) in Route B is greater than 80, 85, 90, 92, 95, or 96%. In some embodiments, the yield is greater than or equal to 97%.

Step (b) of Route B is a de-boc reaction that is performed with an acid. See, Scheme 9.

In some embodiments, the suitable acid used in step (b) is p-toluenesulfonic acid. In some embodiments, the anion (X) is tosylate.

A person or ordinary skill in the art will recognize that the order of addition of compounds and solvents is not required in successfully converting compound C to compound L. Typically, one would admix compound C with an acid, a first organic solvent and water.

The conversion of compound C to compound L according to step (b) of Route B can be carried out at a variety of temperatures. For example, the reaction can be performed at from about 10 to 100° C., from about 30 to 90° C., from about 50 to 80° C., or from about 60 to 70° C. In some embodiments, the temperature of the reaction is about 65° C. A person of skill in the art will recognize the time to complete the reaction will depend on temperature.

The embodiments of step (b) of Route B described herein greatly improve the yield of this conversion. In some embodiments, the yield of step (b) is greater than 70, 80, 85, or 90%. In some embodiments, the yield is greater than or equal to 91%. In contrast, the '006 approach as shown in Scheme 3 produces the free base form of compound B with only a 58.5% yield.

Step (c) of Route B provides a biphasic solvent system comprising water and a second organic solvent which can efficiently convert compound L or a free base thereof to olaparib in a very high yield and purity. In some embodiments, the conversion of step (c) is performed with a second organic solvent, an inorganic base, and cyclopropanecarbonyl chloride. Scheme 10 shows the production of olaparib starting from compound J (a particular compound within the scope of compound L) according to step (c) of Route B. Scheme 10 is shown as an illustrative example of this conversion, and it not meant to limit the scope of the invention in any way.

Scheme 9: Synthesis of compound L from compound C

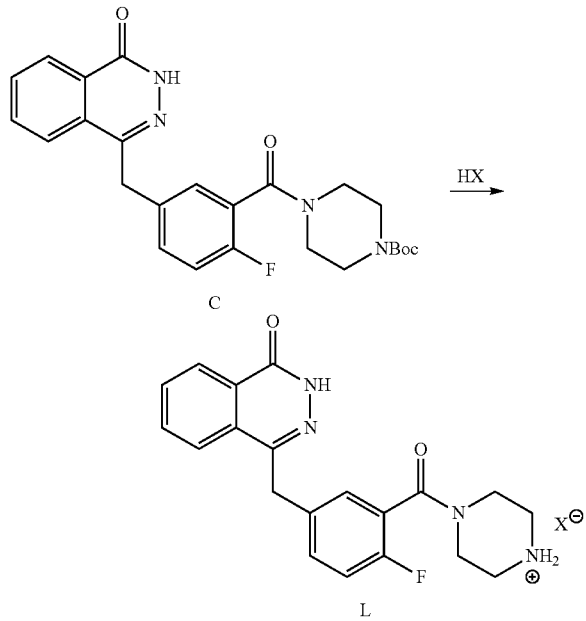

Scheme 10: Synthesis of API from compound J in ethyl acetate/water

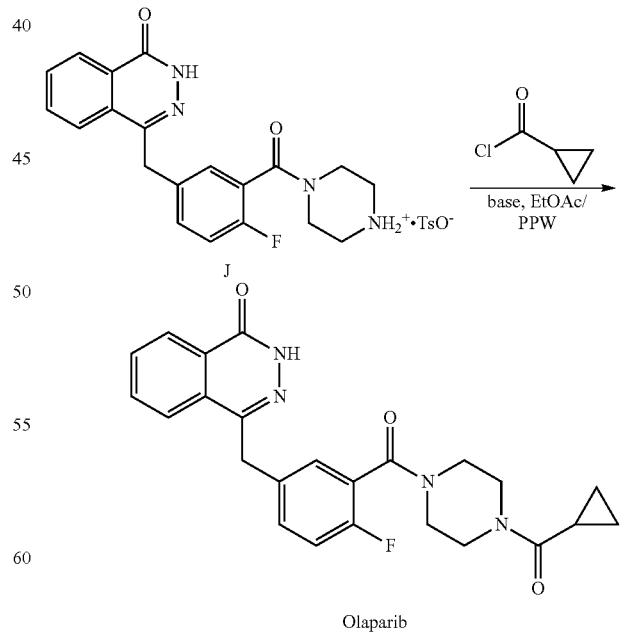

A person or ordinary skill in the art will recognize that the order of addition of compounds and solvents is not required in successfully converting compound L or a free base thereof to olaparib. Typically, one would admix a second organic solvent and water followed by addition compound L or its free base and an inorganic base. After a sufficient amount of time, cyclopropanecarbonyl chloride is added to the reaction mixture. In some embodiments, all compounds and solvents are added at the same time.

The conversion of compound L or a free base thereof to olaparib can be carried out at a variety of temperatures. For example, the reaction can be performed at from about 10 to 100° C., from about 15 to 80° C., from about 17 to 60° C., or from about 20 to 40° C. In some embodiments, the temperature of the reaction is about 25° C. A person of skill in the art will recognize the time to complete the reaction will depend on temperature.

In some embodiments, the olaparib produced via step (c) of Route B has a decreased solubility in the reaction solvent as compared to the starting material. In some embodiments, the reaction is cooled to a lower temperature to facilitate the precipitation of olaparib from the reaction solvent. A lower reaction temperature can include any temperature below 20° C. For example, a lower reaction temperature can include temperatures below 15° C., 10° C., 5° C., 0° C., or −10° C. In some embodiments, the lower reaction temperature is about 0° C.

The conversion of step (c) of Route B can be achieved using a variety of inorganic bases. In some embodiments, the inorganic base used in step (c) is selected from the group consisting of an alkali metal carbonate, an alkali metal bicarbonate, and combinations thereof. In some embodiments, the alkali metal carbonate is selected from the group consisting of $Li_2CO_3$, $Na_2CO_3$, $K_2CO_3$, and combinations thereof. In some embodiments, the alkali metal carbonate is $K_2CO_3$. In some embodiments, the alkali metal bicarbonate is selected from the group consisting of $LiHCO_3$ and $NaHCO_3$.

In some embodiments, the second organic solvent used in step (c) of Route B is a $C_{1-10}$alkyl acetate. In some embodiments, the $C_{1-10}$alkyl acetate is ethyl acetate.

Unlike the method according to the '006 patent, the method according to step (c) of Route B does not require an additional distillation step to remove any solvent in work-up steps. See, Scheme 4. Instead, the products of step (c) (olaparib) precipitate in the biphasic solvent system. This greatly reduces work-up and isolation efforts, greatly improving its industrial applicability. In some embodiments, after the addition of cyclopropanecarbonyl chloride in the two-phase solvent system, a considerable amount of precipitates was observed in few minutes.

The process according to step (c) of Route B can produce high yields and highly pure olaparib. In some embodiments, the yield of step (c) of Route B can be greater than 85, 90, or 95%. In some embodiments, the purity of olaparib obtained in step (c) can be greater than 90, 95, 97, or 99% pure.

In some embodiments, the synthesis of compound L in Route B could be simplified to a single one-pot process, where steps (a) and (b) are performed in a single reaction vessel. The process according to these embodiments removes the need to isolate compound C. Rather than isolating compound C, step (a) and (b) can be merged by the addition of a suitable acid according to step (b) into the reaction mixture of step (a). In some embodiments, the suitable acid is p-toluenesulfonic acid. In some embodiments water is added with the suitable acid.

In some embodiments, the one-pot process of Route B is heated when a suitable acid is added. In some embodiments, the one-pot process is cooled after a suitable amount of time to complete both reactions. A suitable amount of time can be 1, 2, 3, 4 or more hours.

In some embodiments, compound L precipitates from the reaction when the one-pot process is cooled after the reaction is complete. Precipitation of compound L greatly improves the industrial applicability and efficiency of this process.

In one embodiment, while the reaction of compound D with 1-(tert-butoxycarbonyl)piperazine was completed in a reaction mixture with pivaloyl chloride and N,N-diisopropylethylamine (DIPEA), in acetone, p-TSA and water were directly added to the reactor and the resulting mixture was heated to reflux. Subsequently, the reaction was cooled to about 0° C., as a result, the precipitation of compound J was observed. After filtering and washing with acetone, the obtained compound J could be employed to prepare olaparib without any loss of quality.

B. Route A

In accordance with Route A of the present disclosure, the synthesis of olaparib can be performed by
    contacting the 5-[(3,4-dihydro-4-oxo-1-phthalazinyl)methyl]-2-fluorobenzoic acid (compound D):

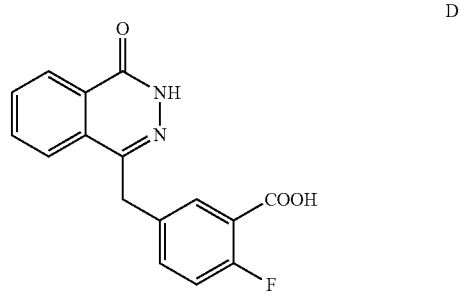 [SMILES: O=C(O)c1cc(Cc2n[nH]c(=O)c3ccccc23)ccc1F]

with N-cyclopropanoyl piperazinium p-toluenesulfonate (compound A)

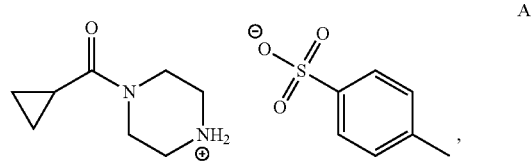

pivaloyl chloride, and a tertiary amine in an organic solvent to afford olaparib.

A person or ordinary skill in the art will recognize that the order of addition of compounds and solvents is not required in successfully converting compound D to olaparib. Typically, one would admix compound D dissolved in an organic solvent with DIPEA and pivaloyl chloride. After a suitable amount of time, compound A is added to this reaction mixture.

The process of Route A can be carried out at a variety of temperatures. For example, the temperature of the reaction mixture when adding compounds and/or solvents can be about 0° C. and after addition of the compounds/solvents the reaction mixture can be about 24° C. In some embodiments, the temperature of the reaction mixture when adding compounds and/or solvents is from about −40 to 20° C. In some embodiments, the temperature when adding compounds and/or solvents is from about −10 to 10° C. In some embodiments, the temperature after adding compounds and/or solvents is from about 10 to 50° C. In some embodiments, the temperature after adding compounds and/or solvents is from about 20 to 30° C.

In accordance with Route A of the present disclosure, p-toluenesulfonic acid (p-TSA) was preferably used as acid source to prepare compound A through a de-Boc reaction of tert-butyl 4-(cyclopropanecarbonyl)piperazine-1-carboxylate. Applicants have surprisingly discovered that, compound A is non-hygroscopic and well-crystallized in comparison with 1-(cyclopropylcarbonyl)piperazine and its mineral acid salt. It has been found that these properties are surprisingly more beneficial for the treatment and storage of compound A in the course of manufacturing olaparib.

HBTU, the coupling agent used in '416 patent, requires a high polar solvent such as acetonitrile to dissolve. In contrast, the process according to Route A uses pivaloyl chloride as a coupling agent. Pivaloyl chloride is much more soluble and can be used in various organic solvents. By switching the coupling agent, the process for producing olaparib disclosed herein removes both the expensive coupling agent, HBTU, as well as the toxic and highly flammable solvent, acetonitrile.

In some embodiments, the organic solvent used in Rout A is a dialkyl ketone. In some embodiments, the dialkyl ketone is selected from the group consisting of acetone, acetophenone, butanone, diethyl ketone, ethyl isopropyl ketone, 2-hexanone, isophorone, mesityl oxide, methyl isobutyl ketone, methylisopropyl ketone, 3-methyl-2-pentanone, 2-pentanone, cyclohexanone, and cyclopetanone. In some embodiments, the dialkyl ketone is acetone.

In some embodiments, the tertiary amine used in Route A is selected from the group consisting of trimethylamine, N,N-diisopropylethylamine (DIPEA), N-methylmorpholine (NMM), tributylamine, 2,2,6,6-tetramethylpiperidine (TMP), pempidine (PMP), 2,6-dimethylpyridine, 2,4,6-trimethylpyridine. In some embodiments, the tertiary amine is N,N-diisopropylethylamine (DIPEA).

In some embodiments, Route A further comprises isolating olaparib. The isolation of olaparib can be performed using various known means in the art. For example, olaparib may be isolated using liquid-liquid extraction. In some embodiments olaparib is isolated by extracting the reaction mixture with an aqueous solvent. In some embodiments the aqueous solvent comprises water, a base, and a salt. In some embodiments the base is NaHCO$_3$ and the salt is NaCl. In some embodiments, the extraction further comprises addition of an organic solvent. In some embodiments the organic solvent is EtOAc.

In some embodiments Route A comprises recrystallizing isolated olaparib. In some embodiments, isolated olaparib is dissolved in a solvent and warmed to an elevated temperature followed by addition of an antisolvent to precipitate olaparib. In some embodiments the solvent is MeOH. In some embodiments, the antisolvent is water. In some embodiments, the elevated temperature is from about 40 to 80° C. In some embodiments, the elevated temperature is 60-70° C. In some embodiments, the elevated temperature is about 65° C. In some embodiments, the solution of solvent and antisolvent is cooled to room temperature facilitate precipitation.

In some embodiments, the yield of recrystallized olaparib produced using Route A is greater than 70%. In some embodiments, the yield of Route A is greater than 75, 80, or 85%. In some embodiments the purity of recrystallized olaparib produced by Route A is greater than 90, 95, 97, or 99%.

An additional advantage to the process of Route A is that pivaloyl chloride can be rapidly quenched with water in work-up steps to generate pivalic acid, which is mild irritant and much less toxic against the human body and the environment. Accordingly, Route A is an improved process for preparing olaparib in comparison with the synthetic routes currently known.

IV. EXAMPLES

The following examples are provided to further illustrate, but not to limit this invention.

Example 1

Preparation of N-cyclopropanoyl piperazinium p-toluenesulfonate (compound A)

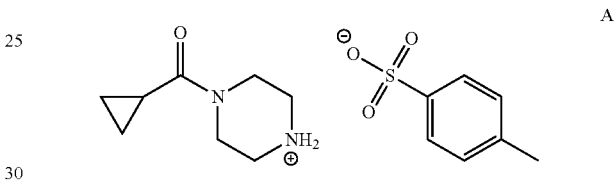

N-Boc-4-cyclopropanoyl piperazine (20.00 g, 78.64 mmol, 1.0 equiv.) and p-toluenesulfonic acid (p-TSA) monohydrate (15.71 g, 82.60 mmol, 1.05 equiv.) and ethyl acetate (EtOAc) (160 mL, 8 vol.) were added to a 3-necked 250 mL flask equipped with 5 cm stir bar, condenser, thermal couple and N$_2$ inlet. The resulting mixture was heated to 50° C. overnight. The reaction was monitored by TLC. Upon completion, the suspension was cooled to 0° C. in ice bath and stirred for 1 hour. After stirring, the resulting slurry was filtered through Buchner funnel. The obtained wet cake was washed with EtOAc (20.0 mL, 1 vol.) twice (and dried at not more than 60° C. under vacuum overnight to afford compound A as white solid (23.12 g, 70.83 mmol, 90.08% Yield).

$^1$H NMR (400 MHz, CDCl$_3$) ☐: 0.75 (m, 2H), 0.94 (m, 2H), 1.61 (m, 1H), 2.35 (s, 3H), 3.23 (br, 4H), 3.86 (br, 4H), 7.19 (d, J=8.2 Hz, 2H), 7.69 (d, J=8.2 Hz, 2H), 9.20 (br, 1H).

Preparation of Olaparib from 5-[(3,4-dihydro-4-oxo-1-phthalazinyl)methyl]-2-fluorobenzoic acid (compound D)

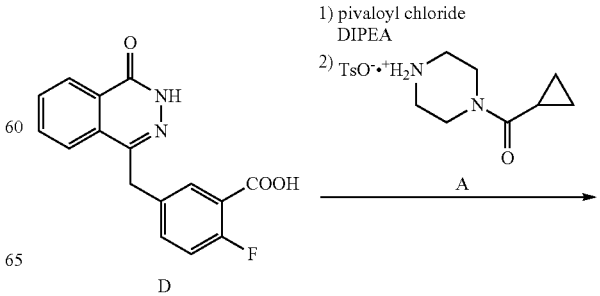

21
-continued

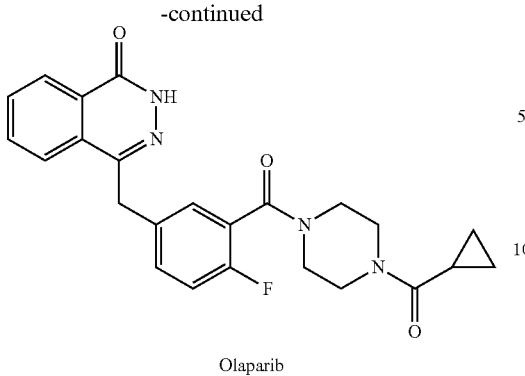

Olaparib

5-[(3,4-dihydro-4-oxo-1-phthalazinyl)methyl]-2-fluorobenzoic acid (compound D) (1.012 g, 3.393 mmol, 1.0 equiv.) and acetone (10.0 mL, 10 vol.) were charged to a 3-neck 50 mL flask equipped with a 2 cm stir bar, thermal couple and $N_2$ inlet. The resulting suspension was cooled to 0° C. N,N-diisopropylethylamine (DIPEA) (0.67 mL, 4.1 mmol, 1.2 equiv.) was added dropwise to the above resulting suspension at 0° C., followed by addition of pivaloyl chloride (0.50 mL, 4.1 mmol, 1.2 equiv.) at 0° C. After the addition, the resulting mixture was warmed to room temperature and stirred for 3 hours. Upon completion, the mixture was cooled to 0° C. N-cyclopropanoyl piperazinium p-toluenesulfonate (compound A) (1.21 g, 4.00 mmol, 1.1 equiv.) was added in portions at 0° C., and then acetone (0.5 mL) was added to rinse. Subsequently, N,N-diisopropylethylamine (DIPEA) (0.83 mL, 5.0 mmol, 1.5 equiv.) was added dropwise to the above flask at 0° C. After the addition, the resulting mixture was warmed to room temperature and stirred for 3 hours. Upon completion, the suspension was diluted with $NaHCO_{3(aq)}$ (20 mL) and EtOAc (20 mL), and then stirred for 1 hour at 0° C. in an ice bath. After stirring, the mixture was filtered through a Buchner funnel to afford off-white solids. The filtrate was extracted with EtOAc (20 mL) three times. The combined organic part was washed with $NaHCO_{3(aq)}$ (20 mL), water (20 mL), and $NaCl_{(aq)}$ (20 mL) to give a clear EtOAc solution. The above resulting off-white solids were combined with the EtOAc solution and concentrated. The resulting solids were dissolved in methanol (MeOH) (25 mL) and stirred at 65° C., followed by slow addition of water (50 mL). The resulting clear solution was cooled to room temperature and stirred overnight. The slurry was filtered through a Buchner funnel. The obtained wet cake was washed with water (25 mL) twice and dried at not more than 60° C. under vacuum overnight to afford olaparib as off-white solid (1.32 g, 3.04 mmol, 89.5% Yield).

$^1$H NMR (400 MHz, DMSO-$d_6$) δ: 0.74 (m, 4H), 1.94 (br, 1H), 3.20 (br, 2H), 3.37-3.75 (m, 6H), 4.33 (s, 2H), 7.24 (t, J=8.8 Hz, 1H), 7.38 (m, 1H), 7.44 (m, 1H), 7.83 (dt, J=7.4 and 0.8 Hz, 1H), 7.89 (t, J=7.1 Hz, 1H), 7.96 (d, J=7.6 Hz, 1H), 8.26 (dd, J=7.9 and 1.0 Hz, 1H), 12.60 (s, 1H).

22

Example 2

Preparation of 4-[2-fluoro-5-(4-oxo-3,4-dihydro-phthalazin-1-ylmethyl)-benzoyl]-piperazin-1-carboxylic acid tert-butyl ester (compound C) from 5-[(3,4-dihydro-4-oxo-1-phthalazinyl)methyl]-2-fluorobenzoic acid (compound D)

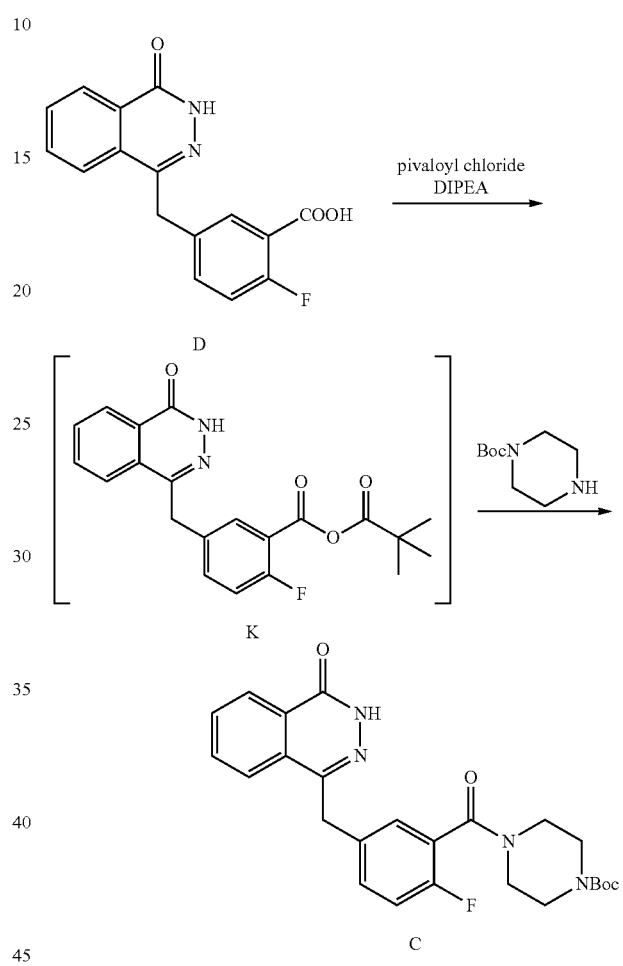

5-[(3,4-dihydro-4-oxo-1-phthalazinyl)methyl]-2-fluorobenzoic acid (compound D) (100.0 g, 335.2 mmol, 1.0 equiv.) and acetone (800.0 mL, 8 vol.) were charged to a 3 L jacket reactor equipped with an overhead stirrer (8 cm stirring blades, agitation speed: 240 rpm), thermal couple and $N_2$ inlet. Pivaloyl chloride (50.0 mL, 402 mmol, 1.2 equiv.) was added over 1 minute at room temperature, and then N,N-diisopropylethylamine (DIPEA) (67.0 mL, 402 mmol, 1.2 equiv.) was added into the above jacket reactor over 10 min at not more than 30° C. After the addition, the resulting solution was stirred for not less than 1 hour at room temperature. Upon completion, 1-(tert-butoxycarbonyl)piperazine (75.0 g, 402 mmol, 1.2 equiv.) was added in one portion into the above jacket reactor at room temperature and acetone (30 mL, 0.3 vol.) was added to rinse. The resulting mixture was stirred at room temperature for not less than 1 hour. When the reaction was completed, water (1600 mL, 16 vol.) was added to the above jacket reactor at room temperature (15 to 25° C.). The resulting mixture was stirred at room temperature for not less than 1 hour and then stirred at 0-5° C. for not less than 2 hours. After stirring, the resulting slurry was filtered through Buchner funnel. The obtained wet cake was washed with water (300.0 mL, 3 vol.) three times and dried at not more than 60° C. under vacuum overnight to afford compound C as off-white solid (151.7 g, 325.2 mmol, 97.00% Yield).

$^1$H NMR (400 MHz, CDCl$_3$) δ: 1.44 (s, 9H), 3.24 (br, 2H), 3.36 (m, 2H), 3.49 (br, 2H), 3.72 (br, 2H), 4.26 (s, 2H), 7.01 (t, J=8.8 Hz, 1H), 7.27-7.31 (m, 2H), 7.69 (m, 1H), 7.72-7.76 (m, 2H), 8.45 (m, 1H), 10.52 (s, 1H).

Example 3

Preparation of 4-[2-fluoro-5-(4-oxo-3,4-dihydro-phthalazin-1-ylmethyl)-benzoyl]-piperazinium p-toluenesulfonate (compound J) from 4-[2-fluoro-5-(4-oxo-3,4-dihydro-phthalazin-1-ylmethyl)-benzoyl]-piperazin-1-carboxylic acid tert-butyl ester (compound C)

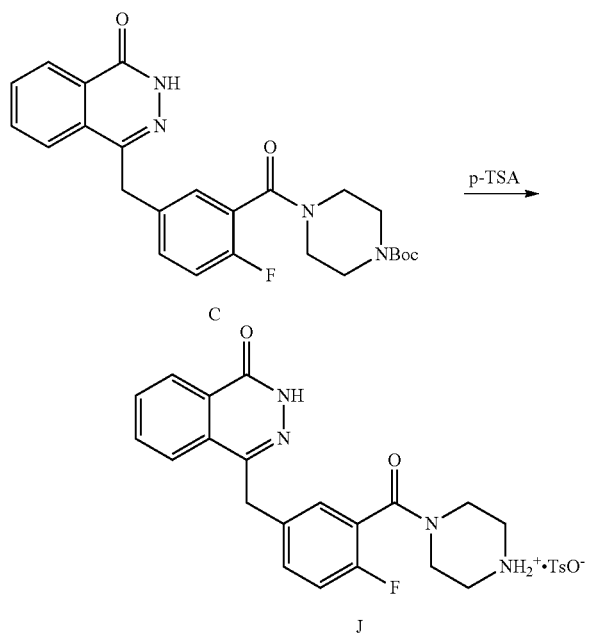

Compound C (3.00 g, 6.43 mmol, 1.0 equiv.), p-toluene-sulfonic acid (p-TSA) monohydrate (2.45 g, 12.9 mmol, 2.0 equiv.), water (2.4 mL, 0.8 vol) and acetone (18.0 mL, 6 vol.) were charged to a 3-neck 100 mL flask equipped with a 2.5 cm stir bar, condenser, thermal couple and N$_2$ inlet. The resulting mixture was heated to reflux for not less than 4 hours (T$_{in}$: 56.9° C., T$_{out}$: 65° C.). Upon completion, acetone (57 mL, 19 vol.) was added. The resulting slurry was cooled to 0° C. and stirred for not less than 2 hours, followed by filtration. The obtained wet cake was washed with acetone (9.0 mL, 3 vol.) for three times and dried at not more than 60° C. under vacuum to afford compound J as off-white solids (3.18 g, 5.90 mmol, 91.20% Yield).

$^1$H NMR (400 MHz, DMSO-d$_6$) δ: 2.28 (s, 3H), 3.01 (br, 2H), 3.19 (m, 2H), 3.42 (br, 2H), 3.79 (br, 2H), 4.33 (s, 2H), 7.11 (d, J=8.4 Hz, 2H), 7.26 (t, J=8.8 Hz, 1H), 7.38 (dd, J=6.4 and 2.0 Hz, 1H), 7.47-7.49 (m, 3H), 7.81-7.96 (m, 3H), 8.25-8.28 (dd, J=7.8 and 1.0 Hz, 1H), 8.79 (br, 2H), 12.60 (s, 1H).

Example 4

One-pot Preparation of 4-[2-fluoro-5-(4-oxo-3,4-dihydro-phthalazin-1-ylmethyl)-benzoyl]-piper-azinium p-toluenesulfonate (compound J) from 5-[(3,4-dihydro-4-oxo-1-phthalazinyl)methyl]-2-fluorobenzoic acid (compound D)

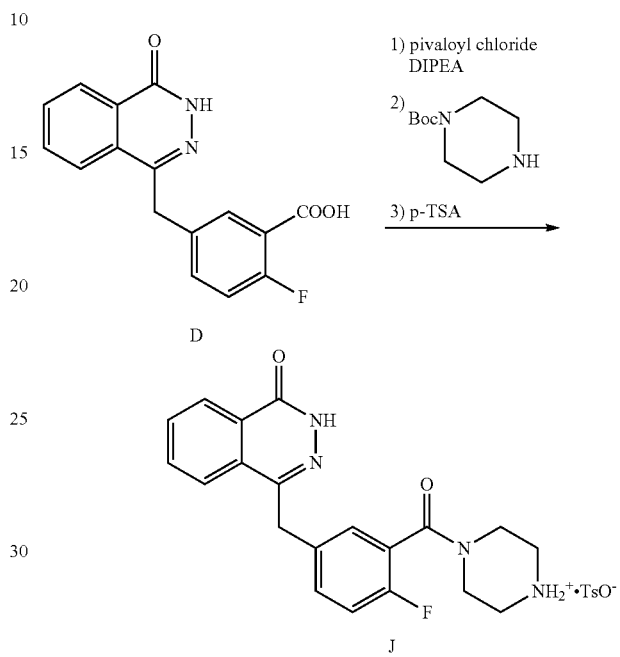

5-[(3,4-dihydro-4-oxo-1-phthalazinyl)methyl]-2-fluorobenzoic acid (compound D) (10.03 g, 33.62 mmol, 1.0 equiv.) and acetone (80.0 mL, 8 vol.) were charged to a 3-neck 250 mL jacket reactor equipped with an overhead stirrer (6 cm stirring blades, agitation speed 246 rpm), thermal couple and N$_2$ inlet. Pivaloyl chloride (4.60 mL, 36.9 mmol, 1.1 equiv.) was added at room temperature. N,N-diisopropylethylamine (DIPEA) (6.1 mL, 36.9 mmol, 1.1 equiv.) was added into the above jacket reactor at not more than 30° C. After the addition, the resulting solution was stirred for not less than 1 hour at room temperature. Upon completion, 1-(tert-butoxycarbonyl)piperazine (7.54 g, 40.5 mmol, 1.2 equiv.) was added into the above jacket reactor at room temperature. The resulting mixture was stirred at room temperature for not less than 1 hour. When the reaction was completed, p-toluenesulfonic acid (p-TSA) monohydrate (19.31 g, 101.5 mmol, 3 equiv.) and water (8 mL, 0.8 vol.) were added to the above jacket reactor at room temperature. The resulting mixture was heated to reflux and stirred for not less than 3 hours (T$_{in}$: 56.9° C., T$_{out}$: 65° C.). Upon completion, acetone (120 mL, 12 vol.) was added. The resulting slurry was cooled to 0° C. and stirred for not less than 1 hour, followed by filtration. The obtained wet cake was washed with acetone (30.0 mL, 3 vol.) three times and dried at NMT 50° C. under vacuum to afford compound J as off-white solids (17.09 g, 31.73 mmol, 94.4% Yield).

$^1$H NMR (400 MHz, DMSO-d$_6$) δ: 2.30 (s, 3H), 3.02 (br, 2H), 3.20 (m, 2H), 3.39 (br, 2H), 3.81 (br, 2H), 4.35 (s, 2H), 7.13 (d, J=8.4 Hz, 2H), 7.27 (t, J=8.8 Hz, 1H), 7.39 (dd, J=6.4 and 2.0 Hz, 1H), 7.47-7.51 (m, 3H), 7.82-7.97 (m, 3H), 8.27-8.29 (dd, J=7.8 and 1.0 Hz, 1H), 8.83 (br, 2H), 12.60 (s, 1H).

Example 5

Preparation of Olaparib from 4-[2-fluoro-5-(4-oxo-3,4-dihydro-phthalazin-1-ylmethyl)-benzoyl]-piperazinium p-toluenesulfonate (compound J)

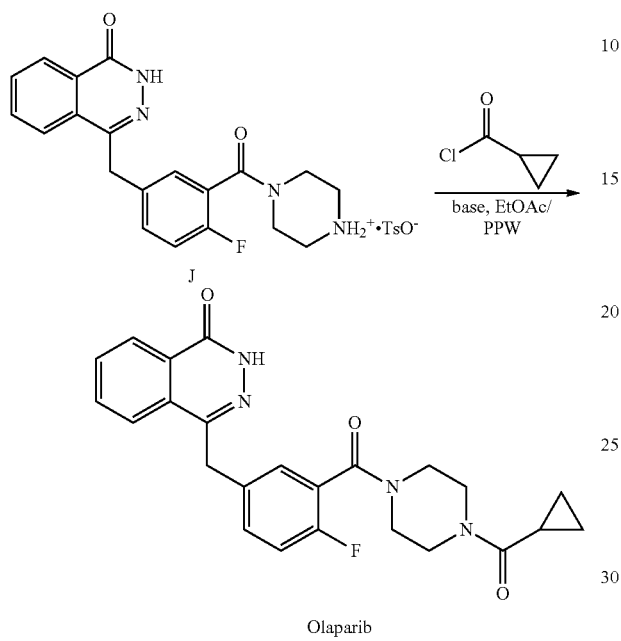

To a 3-neck 50 mL flask equipped with a 2.5 cm stir bar, thermometer and N$_2$ inlet, EtOAc (20 mL, 10 vol) and water (10 mL, 5 vol) were added. And then, compound J (2.01 g, 3.73 mmol, 1.00 equiv.) and K$_2$CO$_3$ (1.54 g, 11.1 mmol, 3.00 equiv.) were added to the above flask. The resulting suspension was stirred at room temperature for not less than 1 hour to form a clear bi-phasic solution. Cyclopropanecarbonyl chloride (0.41 mL, 4.46 mmol, 1.2 equiv.) was added to the above clear solution at room temperature. After the addition, the mixture was stirred at room temperature for 2 hours. Upon completion, the suspension was cooled to about 0° C. and stirred for additional 2 hours. The suspension was filtered through a Buchner funnel to give a pale-yellow cake. The pale-yellow cake was washed with water (6.0 mL, 3 vol.) for three times and EtOAc (4 mL, 2 vol.) once, and then dried at not more than 60° C. under vacuum to afford olaparib (1.60 g, 3.68 mmol, 98.7% Yield).

$^1$H NMR (400 MHz, DMSO-d$_6$) δ: 0.74 (m, 4H), 1.94 (br, 1H), 3.19 (br, 2H), 3.37-3.74 (m, 6H), 4.33 (s, 2H), 7.24 (t, J=8.8 Hz, 1H), 7.37 (m, 1H), 7.44 (m, 1H), 7.83 (dt, J=7.4 and 0.8 Hz, 1H), 7.89 (t, J=7.1 Hz, 1H), 7.96 (d, J=7.6 Hz, 1H), 8.26 (dd, J=7.9 and 1.0 Hz, 1H), 12.59 (s, 1H)

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing 4-[(3-[(4-cyclopropylcarbonyl) piperazin-1-yl]carbonyl)-4-fluorophenyl]methyl(2H) phthalazin-1-one (Olaparib)

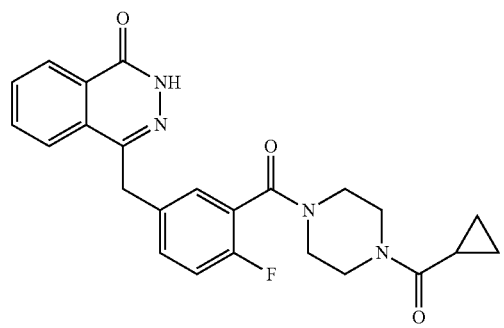 [SMILES: O=C(c1cc(Cc2n[nH]c(=O)c3ccccc23)ccc1F)N1CCN(C(=O)C2CC2)CC1]

comprising the steps of:
(a) contacting 5-[(3,4-dihydro-4-oxo-1-phthalazinyl) methyl]-2-fluorobenzoic acid (compound D):

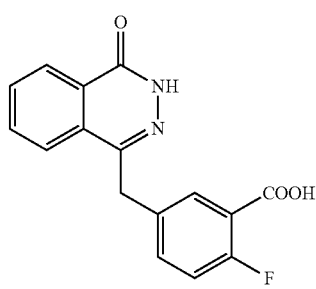

with 1-(tert-butoxycarbonyl)piperazine, pivaloyl chloride and a tertiary amine in a first organic solvent to provide compound C

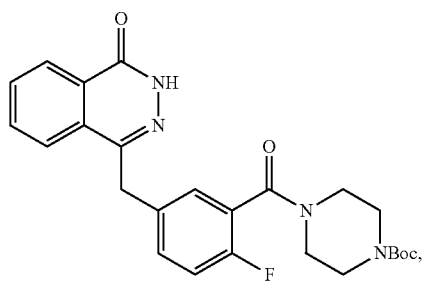

wherein the first organic solvent is selected from the group consisting of acetone, acetophenone, butanone, diethyl ketone, ethyl isopropyl ketone, 2-hexanone, isophorone, mesityl oxide, methyl isobutyl ketone, methyl isopropyl ketone, 3-methyl-2-pentanone, 2-pentanone, cyclohexanone, and cyclopentanone;

(b) contacting compound C and an acid to provide compound L

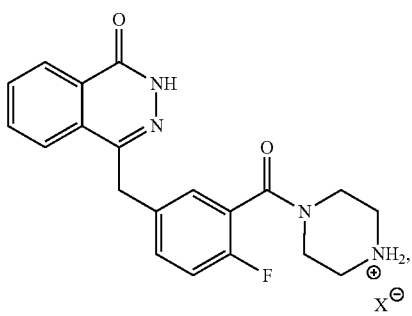

wherein the acid is p-toluenesulfonic acid and X is tosylate; and (c) contacting compound L with cyclopropanecarbonyl chloride and an inorganic base in a biphasic reaction system comprising water and a second organic solvent to afford olaparib, wherein the inorganic base used is selected from the group consisting of an alkali metal carbonate, an alkali metal bicarbonate, and combinations thereof; and the second organic solvent is a $C_{1-10}$alkyl acetate.

2. The process of claim 1, wherein the tertiary amine is selected from the group consisting of trimethylamine, N,N-diisopropylethylamine (DIPEA), N-methylmorpholine (NMM), tributylamine, 2,2,6,6-tetramethylpiperidine (TMP), pempidine (PMP), 2,6-dimethylpyridine, and 2,4,6-trimethylpyridine.

3. The process of claim 2, wherein the tertiary amine is N,N-diisopropylethylamine (DIPEA).

4. The process of claim 1, wherein the first organic solvent is acetone.

5. The process of claim 1, wherein the alkali metal carbonate is selected from the group consisting of $Li_2CO_3$, $Na_2CO_3$, $K_2CO_3$, and combinations thereof.

6. The process of claim 5, wherein the alkali metal carbonate is $K_2CO_3$.

7. The process of claim 1, wherein the alkali metal bicarbonate is selected from the group consisting of $LiHCO_3$, $NaHCO_3$, and combinations thereof.

8. The process of claim 1, wherein the $C_{1-10}$alkyl acetate is ethyl acetate.

9. The process of claim 1, wherein steps (a) and (b) are performed in a single reaction vessel.

10. The process of claim 9, wherein after step (a), said acid is directly added to said reaction vessel to provide compound L.

11. A process for preparing 4-[(3-[(4-cyclopropylcarbonyl)piperazin-1-yl]carbonyl)-4-fluorophenyl]methyl(2H) phthalazin-1-one (Olaparib)

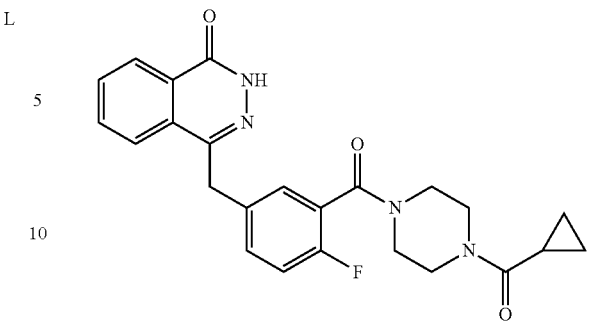

comprising contacting the 5-[(3,4-dihydro-4-oxo-1-phthalazinyl)methyl]-2-fluorobenzoic acid (compound D):

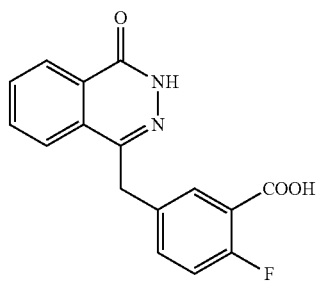

with N-cyclopropanoyl piperazinium p-toluenesulfonate (compound A)

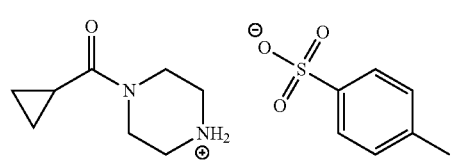

pivaloyl chloride and a tertiary amine in an organic solvent to afford olaparib.

12. The process of claim 11, wherein the tertiary amine is selected from the group consisting of trimethylamine, N,N-diisopropylethylamine (DIPEA), N-methylmorpholine (NMM), tributylamine, 2,2,6,6-tetramethylpiperidine (TMP), pempidine (PMP), 2,6-dimethylpyridine, 2,4,6-trimethylpyridine, and combinations thereof.

13. The process of claim 12, wherein the tertiary amine is N,N-diisopropylethylamine (DIPEA).

14. The process of claim 11, wherein the organic solvent is selected from the group consisting of acetone, acetophenone, butanone, diethyl ketone, ethyl isopropyl ketone, 2-hexanone, isophorone, mesityl oxide, methyl isobutyl ketone, methyl isopropyl ketone, 3-methyl-2-pentanone, 2-pentanone, cyclohexanone, and cyclopentanone.

15. The process of claim 14, wherein the organic solvent is acetone.

* * * * *